United States Patent
Anderson

(10) Patent No.: US 6,433,159 B1
(45) Date of Patent: *Aug. 13, 2002

(54) COMPOSITIONS AND METHODS FOR TREATMENT OF HEPATITIS C VIRUS ASSOCIATED DISEASES

(75) Inventor: Kevin P. Anderson, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/823,895

(22) Filed: Mar. 17, 1997

Related U.S. Application Data

(63) Continuation of application No. 08/453,085, filed on May 30, 1995, now abandoned, which is a continuation of application No. 07/945,289, filed on Sep. 10, 1992, now abandoned.

(51) Int. Cl.[7] .............................................. C07H 21/04
(52) U.S. Cl. ..................................... 536/24.5; 536/23.1
(58) Field of Search ............................... 536/24.5, 23.1, 536/24.1, 24.3, 24.31, 24.32, 24.33; 435/6, 172.3; 514/44; 935/9, 11, 34

(56) References Cited

U.S. PATENT DOCUMENTS

| 5,034,506 A | | 7/1991 | Summerton et al. | |
| 5,427,909 A | * | 6/1995 | Okamoto et al. | ............. 435/54 |

FOREIGN PATENT DOCUMENTS

| EP | 318216 | 11/1988 |
| EP | 419182 | 9/1990 |

OTHER PUBLICATIONS

Choo et al., "Genetic organization and diversity of the hepatitis C virus" *Proc. Natl. Acad. Sci.* 1991, 88, 2451–2455.
Choo et al., "Isolation of a cDNA Clone Derived from a Blood–Borne Non–A, Non–B Viral Hepatitis Genome", *Science*, 1989, 244, 359–362.
Han et al., "Characterization of the terminal regions of hepatitis C viral RNA: Identification of conserved sequences in the 5' untranslated region and poly( A) tails at the 3'end", *Proc. Natl. Acad. Sci*, 1991, 88 , 1711–1715.
Inchauspe et al., "Genomic structure of the human prototype strain H of hepatitis C virus: Comparison with American and Japanese isolates", *Proc. Natl. Acad. Sci.* 1991, 88, 10292–10296.
Nielsen, P.E. et al., "Sequence–Selective Recognition of DNA by Strand Displacement with a Thymine–Substituted Polyamide", *Science* 1991, 254, 1497.
Rothenberg et al., "Oligodeoxynucleotides as Anti–Sense Inhibitors of Gene Expression: Therapeutic Implications", *J. Natl. Cancer Inst.* 1989, 81, 1539–1544.
Takamizawa et al., "Structure and Organization of the Hepatitis C Virus Genome Isolated from Human Carriers", *J. Virol.* 1991, 65, 1105–1113.
Zon, G., "Oligonucleotide Analogues as Potential Chemotherapeutic Agents", *Pharmaceutical Res.* 1987, 5, 539–549.
E. Uhlmann et al., Chem. Rev. 90(4) (6/90) 543–84.*
J. Milligan et al., J. Med. Chem., 36(14) (Jul. 9, 1993), 1924–37.*
C. Szein et al., Science, 261 (Aug. 20, 1993) 1004–1012.*
B. Tseng et al., Cancer Gene Therapy 1(1) (3/94) 65–71.*
P. Westermann et al., Biomed. Biochim Acta 48(1) (89) 85–93.*
W. James, Antiviral Chem. & Chemother., 2(4) ('91) 191–214.*
C. Smith et al., PNAS 83 (May '86) 2787–91.*
G. Goodarzi et al., J. Gen. Virol. 71 (90) 3021–25.*
E. Wicksaram et al., FASEB J., vol. 5 (5) (Mar. 15, 1991) A1443.

* cited by examiner

*Primary Examiner*—Andrew Wang
(74) *Attorney, Agent, or Firm*—Licata & Tyrrell P.C.

(57) ABSTRACT

Antisense oligonucleotides are provided which are complementary to at least a portion of HCV RNA and specifically hybridizable therewith. These oligonucleotides can be administered to inhibit the replication of Hepatitis C virus in vivo or in vitro and to treat Hepatitis C virus-associated disease. These compounds can be used either prophylactically or therapeutically to reduce the severity of diseases associated with Hepatitis C virus.

1 Claim, No Drawings

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
      (A) LENGTH: 21
      (B) TYPE: Nucleic
      (C) STRANDEDNESS: Single
      (D) TOPOLOGY: Linear (iv) ANTI-SENSE: Yes (xi) SEQUENCE DESCRIPTION: SEQ ID NO: 1:

ATGGTGGAGT GTCGCCCCGT C                21

(2) INFORMATION FOR SEQ ID NO: 2:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION:  SEQ ID NO: 2:

GGAGTGATCT ATGGTGGAGT G                                                  21

(2) INFORMATION FOR SEQ ID NO: 3:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION:  SEQ ID NO: 3:

GATTCGTGCT CATGGTGCAC G                                                  21

(2) INFORMATION FOR SEQ ID NO: 4:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION:  SEQ ID NO: 4:

TCCAGGCATT GAGCGGGTTG A                                                  21

(2) INFORMATION FOR SEQ ID NO: 5:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION:  SEQ ID NO: 5:

TGGCCTGGAG TGTTTATCTC C                                                  21

(2) INFORMATION FOR SEQ ID NO: 6:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION:  SEQ ID NO: 6:

GGGGTAGGCA TCTACCTGCT C                                                  21

(2) INFORMATION FOR SEQ ID NO: 7:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 7:

CGCCCCCATC AGGGGGCTGG C                                              21

(2) INFORMATION FOR SEQ ID NO: 8:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 8:

TTCATGGTGG AGTGTCGCCC C                                              21

(2) INFORMATION FOR SEQ ID NO: 9:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 9:

GTTCCTCACA GGGGAGTGAT T                                              21

(2) INFORMATION FOR SEQ ID NO: 10:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 10:

TACTAACGCC ATGGCTAGAC G                                              21

(2) INFORMATION FOR SEQ ID NO: 11:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 11:

CTATGGCTCT CCCGGGAGGG G                                              21

(2) INFORMATION FOR SEQ ID NO: 12:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 12:

CCACTATGGC TCTCCCGGGA G                                              21

(2) INFORMATION FOR SEQ ID NO: 13:

(i) SEQUENCE CHARACTERISTICS:
        (A) LENGTH: 21

(B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 13:

CGGTGTACTC ACCGGTTCCG C                                              21

(2) INFORMATION FOR SEQ ID NO: 14:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 14:

CTGGCAATTC CGGTGTACTC A                                              21

(2) INFORMATION FOR SEQ ID NO: 15:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 15:

GGGGCACGCC CAAATCTCCA G                                              21

(2) INFORMATION FOR SEQ ID NO: 16:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 16:

CCTTTCGCGA CCCAACACTA C                                              21

(2) INFORMATION FOR SEQ ID NO: 17:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 17:

CCCTATCAGG CAGTACCACA A                                              21

(2) INFORMATION FOR SEQ ID NO: 18:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 18:

CTCCCGGGGC ACTCGCAAGC A                                              21

(2) INFORMATION FOR SEQ ID NO: 19:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 19:

CATGGTGCAC GGTCTACGAG A                                              21

(2) INFORMATION FOR SEQ ID NO: 20:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 20:

GATTCGTGCT CATGGTGCAC G                                              21

(2) INFORMATION FOR SEQ ID NO: 21:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 21:

TTTAGGATTC GTGCTCATGG T                                              21

(2) INFORMATION FOR SEQ ID NO: 22:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 22:

GAGTGGTTAG CCCAATCTTC A                                              21

(2) INFORMATION FOR SEQ ID NO: 23:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 23:

TATTGGCCTG GAGTGGTTAG C                                              21

(2) INFORMATION FOR SEQ ID NO: 24:

(i) SEQUENCE CHARACTERISTICS:
        (A) LENGTH: 21
        (B) TYPE: Nucleic
        (C) STRANDEDNESS: Single
        (D) TOPOLOGY: Linear (iv) ANTI-SENSE: Yes (xi) SEQUENCE DESCRIPTION: SEQ ID NO: 24:

AGGGAATGGC CTATTGGCCT G       21

(2) INFORMATION FOR SEQ ID NO: 25:

(i) SEQUENCE CHARACTERISTICS:
        (A) LENGTH: 9401
        (B) TYPE: Nucleic
        (C) STRANDEDNESS: Single
        (D) TOPOLOGY: Linear (iv) ANTI-SENSE: NO (xi) SEQUENCE DESCRIPTION: SEQ ID NO: 25:

| | | |
|---|---|---|
| gccagcccc tgatgggggc gacactccac catgaatcac tccctgtga | 50 |
| ggaactactg tcttcacgca gaaagcgtct agccatggcg ttagtatgag | 100 |
| tgtcgtgcag cctccaggac ccccctccc gggagagcca tagtggtctg | 150 |
| cggaaccggt gagtacaccg gaattgccag gacgaccggg tcctttcttg | 200 |
| gatcaacccg ctcaatgcct ggagatttgg gcgtgccccc gcaagactgc | 250 |
| tagccgagta gtgttgggtc gcgaaaggcc ttgtggtact gcctgatagg | 300 |
| gtgcttgcga gtgccccggg aggtctcgta accgtgcac catgagcacg | 350 |
| aatcctaaac ctcaaaaaaa aaacaaacgt aacaccaacc gtcgcccaca | 400 |
| ggacgtcaag ttcccgggtg gcggtcagat cgttggtgga gtttacttgt | 450 |
| tgccgcgcag gggccctaga ttgggtgtgc gcgcgacgag aaagacttcc | 500 |
| gagcggtcgc aacctcgagg tagacgtcag cctatcccca aggctcgtcg | 550 |
| gcccgagggc aggacctggg ctcagcccgg gtacccttgg ccctctatg | 600 |
| gcaatgaggg ctgcgggtgg gcgggatggc tcctgtctcc ccgtggctct | 650 |
| cggcctagct ggggccccac agaccccgg cgtaggtcgc gcaatttggg | 700 |
| taaggtcatc gataccctta cgtgcggctt cgccgacctc atggggtaca | 750 |
| taccgctcgt cggcgcccct cttggaggcg ctgccagggc cctggcgcat | 800 |
| ggcgtccggg ttctggaaga cggcgtgaac tatgcaacag gaaccttcc | 850 |
| tggttgctct ttctctatct tccttctggc cctgctctct tgcttgactg | 900 |
| tgcccgcttc ggcctaccaa gtgcgcaact ccacggggct ttaccacgtc | 950 |
| accaatgatt gccctaactc gagtattgtg tacgaggcgg ccgatgccat | 1000 |
| cctgcacact ccggggtgcg tcccttgcgt tcgtgagggc aacgcctcga | 1050 |
| ggtgttgggt ggcgatgacc cctacggtgg ccaccaggga tggcaaactc | 1100 |
| cccgcgacgc agcttcgacg tcacatcgat ctgcttgtcg ggagcgccac | 1150 |
| cctctgttcg gccctctacg tgggggacct atgcgggtct gtctttcttg | 1200 |
| tcggccaact gttcaccttc tctcccaggc gccactggac gacgcaaggt | 1250 |
| tgcaattgct ctatctatcc cggccatata acgggtcacc gcatggcatg | 1300 |
| ggatatgatg atgaactggt cccctacgac ggcgttggta atggctcagc | 1350 |
| tgctccggat cccacaagcc atcttggaca tgatcgctgg tgctcactgg | 1400 |
| ggagtcctgg cggcatagc gtatttctcc atggtgggga actgggcgaa | 1450 |
| ggtcctggta gtgctgctgc tatttgccgg cgtcgacgcg gaaacccacg | 1500 |
| tcaccggggg aagtgccggc cacactgtgt ctggatttgt tagcctcctc | 1550 |

| | |
|---|---|
| gcaccaggcg ccaagcagaa cgtccagctg atcaacacca acggcagttg | 1600 |
| gcacctcaat agcacggccc tgaactgcaa tgatagcctc aacaccggct | 1650 |
| ggttggcagg gctttctat caccacaagt tcaactcttc aggctgtcct | 1700 |
| gagaggctag ccagctgccg accccttacc gattttgacc agggctgggg | 1750 |
| ccctatcagt tatgccaacg gaagcggccc cgaccagcgc ccctactgct | 1800 |
| ggcactaccc cccaaaacct tgcggtattg tgcccgcgaa gagtgtgtgt | 1850 |
| ggtccggtat attgcttcac tcccagcccc gtggtggtgg gaacgaccga | 1900 |
| caggtcgggc gcgcccacct acagctgggg tgaaaatgat acggacgtct | 1950 |
| tcgtccttaa caataccagg ccaccgctgg gcaattggtt cggttgtacc | 2000 |
| tggatgaact caactggatt caccaaagtg tgcggagcgc ctccttgtgt | 2050 |
| catcggaggg gcgggcaaca acaccctgca ctgccccact gattgcttcc | 2100 |
| gcaagcatcc ggacgccaca tactctcggt gcggctccgg tccctggatc | 2150 |
| acacccaggt gcctggtcga ctaccgtat aggctttggc attatccttg | 2200 |
| taccatcaac tacaccatat ttaaaatcag gatgtacgtg ggagggggtcg | 2250 |
| aacacaggct ggaagctgcc tgcaactgga cgcggggcga acgttgcgat | 2300 |
| ctggaagaca gggacaggtc cgagctcagc ccgttactgc tgaccactac | 2350 |
| acagtggcag gtcctcccgt gttccttcac aaccctacca gccttgtcca | 2400 |
| ccggcctcat ccacctccac cagaacattg tggacgtgca gtacttgtac | 2450 |
| ggggtggggt caagcatcgc gtcctgggcc attaagtggg agtacgtcgt | 2500 |
| tctcctgttc cttctgcttg cagacgcgcg cgtctgctcc tgcttgtgga | 2550 |
| tgatgctact catatcccaa gcggaggcgg cttttggagaa cctcgtaata | 2600 |
| cttaatgcag catccctggc cgggacgcac ggtcttgtat ccttcctcgt | 2650 |
| gttcttctgc tttgcatggt atttgaaggg taagtgggtg cccggagcgg | 2700 |
| tctacacctt ctacgggatg tggcctctcc tcctgctcct gttggcgttg | 2750 |
| ccccagcggg cgtacgcgct ggacacggag gtggccgcgt cgtgtggcgg | 2800 |
| tgttgttctc gtcgggttga tggcgctgac tctgtcacca tattacaagc | 2850 |
| gctatatcag ctggtgcttg tggtggcttc agtattttct gaccagagtg | 2900 |
| gaagcgcaac tgcacgtgtg gattcccccc ctcaacgtcc gaggggggcg | 2950 |
| cgacgccgtc atcttactca tgtgtgctgt acacccgact ctggtatttg | 3000 |
| acatcaccaa attgctgctg gccgtcttcg gaccccttg gattcttcaa | 3050 |
| gccagtttgc ttaaagtacc ctactttgtg cgcgtccaag gccttctccg | 3100 |
| gttctgcgcg ttagcgcgga agatgatcgg aaggccattac gtgcaaatgg | 3150 |
| tcatcattaa gttaggggcg cttactggca cctatgttta taaccatctc | 3200 |
| actcctcttc gggactgggc gcacaacggc ttgcagatc tggccgtggc | 3250 |
| tgtagagcca gtcgtcttct cccaaatgga gaccaagctc atcacgtggg | 3300 |
| gggcagatac cgccgcgtgc ggtgacatca tcaacgcctt gcctgtttcc | 3350 |
| gccccgcaggg gccgggagat actgctcggg ccagccgatg gaatggtctc | 3400 |
| caagggggtgg aggttgctgg cgcccatcac ggcgtacgcc cagcagacaa | 3450 |
| ggggcctcct agggtgcata atcaccagcc taactggccg ggacaaaaac | 3500 |

```
caagtggagg gtgaggtcca gattgtgtca actgctgccc aaaccttcct      3550
ggcaacgtgc atcaatgggg tgtgctggac tgtctaccac ggggccggaa      3600
cgaggaccat cgccgtcaccc aagggtcctg tcatccagat gtataccaat    3650
gtagaccaag accttgtggg ctggcccgct ccgcaaggta gccgctcatt      3700
gacaccctgc acttgcggct cctcggacct ttacctggtc acgaggcacg      3750
ccgatgtcat tcccgtgcgc cggcggggtg atagcagggg cagcctgctg      3800 tcgcccggc ccatttccta cttgaaaggc tcctcggggg gtccgctgtt       3850
gtgccccgcg gggcacgccg tgggcatatt tagggccgcg gtgtgcaccc      3900
gtggagtggc taaggcggtg gactttatcc ctgtggagaa cctagagaca      3950
accatgaggt ccccggtgtt cacggataac tcctctccac cagtagtgcc      4000
ccagagcttc caggtggctc acctccatgc tcccacaggc agcggcaaaa      4050
gcaccaaggt cccggctgca tatgcagctc agggctataa ggtgctagta      4100
ctcaacccct ctgttgctgc aacactgggc tttggtgctt acatgtccaa      4150
ggctcatggg atcgatccta acatcaggac cggggtgaga acaattacca      4200
ctggcagccc catcacgtac tccacctacg gcaagttcct tgccgacggc      4250
gggtgctcgg ggggcgctta tgacataata atttgtgacg agtgccactc      4300
cacggatgcc acatccatct tgggcatcgg cactgtcctt gaccaagcag      4350
agactgcggg ggcgagactg gttgtgctcg ccaccgccac ccctccgggc      4400
tccgtcactg tgccccatcc caacatcgag gaggttgctc tgtccaccac      4450
cggagagatc cctttttacg gcaaggctat cccctcgaa gtaatcaagg      4500 gggggagaca tctcatcttc tgtcattcaa agaagaagtg cgacgaactc      4550
gccgcaaagc tggtcgcatt gggcatcaat gccgtggcct actaccgcgg      4600
tcttgacgtg tccgtcatcc cgaccagcgg cgatgttgtc gtcgtggcaa      4650
ccgatgccct catgaccggc tataccggcg acttcgactc ggtgatagac      4700
tgcaatacgt gtgtcaccca gacagtcgat ttcagccttg accctacctt      4750
caccattgag acaatcacgc tcccccagga tgctgtctcc cgcactcaac      4800
gtcggggcag gactggcagg gggaagccag gcatctacag atttgtggca      4850
ccgggggagc gcccctccgg catgttcgac tcgtccgtcc tctgtgagtg      4900
ctatgacgca ggctgtgctt ggtatgagct cacgcccgcc gagactacag      4950
ttaggctacg agcgtacatg aacacccgg ggcttcccgt gtgccaggac      5000
catcttgaat tttgggaggg cgtctttaca ggcctcactc atatagatgc      5050
ccactttcta tcccagacaa agcagagtgg ggagaaccttcc ccttacctgg    5100 tagcgtacca agccaccgtg tgcgctaggg ctcaagcccc tcccccatcg     5150
tgggaccaga tgtggaagtg tttgattcgc ctcaagccca ccctccatgg     5200
gccaacaccc ctgctataca gactgggcgc tgttcagaat gaaatcaccc     5250
tgacgcaccc agtcaccaaa tacatcatga catgcatgtc ggccgacctg     5300
gaggtcgtca cgagcacctg ggtgctcgtt ggcggcgtcc tggctgcttt     5350
ggccgcgtat tgcctgtcaa caggctgcgt ggtcatagtg ggcagggtcg     5400
tcttgtccgg gaagccggca atcatacctg acagggaagt cctctaccga     5450
gagttcgatg agatggaaga gtgctctcag cacttaccgt acatcgagca     5500
```

```
agggatgatg ctcgccgagc agttcaagca gaaggccctc ggcctcctgc      5550
agaccgcgtc ccgtcaggca gaggttatcg cccctgctgt ccagaccaac      5600
tggcaaaaac tcgagacctt ctgggcgaag catatgtgga acttcatcag      5650
tgggatacaa tacttggcgg gcttgtcaac gctgctggt  aaccccgcca      5700 ttgcttcatt gatggctttt acagctgctg tcaccagccc actaaccact      5750
agccaaaccc tcctcttcaa catattgggg gggtgggtgg ctgcccagct      5800
cgccgccccc ggtgccgcta ctgcctttgt gggcgctggc ttagctggcg      5850
ccgccatcgg cagtgttgga ctggggaagg tcctcataga catccttgca      5900
gggtatggcg cgggcgtggc gggagctctt gtggcattca agatcatgag      5950
cggtgaggtc ccctccacgg aggacctggt caatctactg cccgccatcc      6000
tctcgcccgg agccctcgta gtcggcgtgg tctgtgcagc aatactgcgc      6050
cggcacgttg gcccgggcga gggggcagtg cagtggatga accggctgat      6100
agccttcgcc tcccggggga accatgtttc ccccacgcac tacgtgccgg      6150
agagcgatgc agctgcccgc gtcactgcca tactcagcag cctcactgta      6200
acccagctcc tgaggcgact gcaccagtgg ataagctcgg agtgtaccac      6250
tccatgctcc ggttcctggc taagggacat ctgggactgg atatgcgagg      6300
tgttgagcga ctttaagacc tggctaaaag ctaagctcat gccacagctg      6350
cctgggatcc ccttttgtgtc ctgccagcgc gggtataagg gggtctggcg      6400
agtggacggc atcatgcaca ctcgctgcca ctgtggagct gagatcactg      6450
gacatgtcaa aaacgggacg atgaggatcg tcggtcctag gacctgcagg      6500
aacatgtgga gtgggacctt ccccattaat gcctacacca cgggcccctg      6550
tacccccctt cctgcgccga actacacgtt cgcgctatgg agggtgtctg      6600
cagaggaata tgtggagata aggcaggtgg gggacttcca ctacgtgacg      6650
ggtatgacta ctgacaatct caaatgcccg tgccaggtcc catcgcccga      6700
atttttcaca gaattggacg gggtgcgcct acataggttt gcgcccccct      6750
gcaagccctt gctgcgggag gaggtatcat tcagagtagg actccacgaa      6800
tacccggtag gtcgcaatt  accttgcgag cccgaaccgg acgtggccgt      6850
gttgacgtcc atgctcactg atccctccca tataacagca gaggcggccg      6900
ggcgaaggtt ggcgagggga tcaccccct  ctgtggccag ctcctcggct      6950
agccagctat ccgctccatc tctcaaggca acttgcaccg ctaaccatga      7000
ctcccctgat gctgagctca tagaggccaa cctcctatgg aggcaggaga      7050
tgggcggcaa catcaccagg gttgagtcag aaaacaaagt ggtgattctg      7100
gactccttcg atccgcttgt ggcggaggag gacgagcggg agatctccgt      7150
acccgcagaa atcctgcgga agtctcggag attcgcccag gccctgcccg      7200
tttgggcgcg gccggactat aaccccccgc tagtggagac gtggaaaaag      7250
cccgactacg aaccacctgt ggtccatggc tgtccgcttc cacctccaaa      7300
gtcccctcct gtgcctccgc ctcggaagaa gcggacggtg tcctcactg      7350 aatcaaccct atctactgcc ttggccgagc tcgccaccag aagctttggc      7400
agctcctcaa cttccggcat tacgggcgac aatacgacaa catcctctga      7450
```

-continued

| | |
|---|---|
| gcccgcccct tctggctgcc ccccgactc cgacgctgag tcctattcct | 7500 |
| ccatgccccc cctggagggg gagcctgggg atccggatct tagcgacggg | 7550 |
| tcatggtcaa cggtcagtag tgaggccaac gcggaggatg tcgtgtgctg | 7600 |
| ctcaatgtct tactcttgga caggcgcact cgtcaccccg tgcgccgcgg | 7650 |
| aagaacagaa actgcccatc aatgcactaa gcaactcgtt gctacgtcac | 7700 |
| cacaatttgg tgtattccac cacctcacgc agtgcttgcc aaaggcagaa | 7750 |
| gaaagtcaca tttgacagac tgcaagttct ggacagccat taccaggacg | 7800 |
| tactcaagga ggttaaagca gcggcgtcaa aagtgaaggc taacttgcta | 7850 |
| tccgtagagg aagcttgcag cctgacgccc ccacactcag ccaaatccaa | 7900 |
| gtttggttat ggggcaaaag acgtccgttg ccatgccaga aaggccgtaa | 7950 |
| cccacatcaa ctccgtgtgg aaagaccttc tggaagacaa tgtaacacca | 8000 |
| atagacacta ccatcatggc taagaacgag gttttctgcg ttcagcctga | 8050 |
| gaaggggggt cgtaagccag ctcgtctcat cgtgttcccc gatctgggcg | 8100 |
| tgcgcgtgtg cgaaaagatg gctttgtacg acgtggttac aaagctcccc | 8150 |
| ttggccgtga tgggaagctc ctacggattc aatactcac caggacagcg | 8200 |
| ggttgaattc ctcgtgcaag cgtggaagtc caagaaaacc ccaatgggt | 8250 |
| tctcgtatga tacccgctgc tttgactcca cagtcactga gagcgacatc | 8300 |
| cgtacggagg aggcaatcta ccaatgttgt gacctcgacc cccaagcccg | 8350 |
| cgtggccatc aagtccctca ccgagaggct ttatgttggg ggccctctta | 8400 |
| ccaattcaag gggggagaac tgcggctatc gcaggtgccg cgcgagcggc | 8450 |
| gtactgacaa ctagctgtgg taacaccctc acttgctaca tcaaggcccg | 8500 |
| ggcagcctgt cgagccgcag ggctccagga ctgcaccatg ctcgtgtgtg | 8550 |
| gcgacgactt agtcgttatc tgtgaaagcg cgggggtcca ggaggacgcg | 8600 |
| gcgagcctga gagccttcac ggaggctatg accaggtact ccgcccccc | 8650 |
| tggggacccc ccacaaccag aatacgactt ggagctcata acatcatgct | 8700 |
| cctccaacgt gtcagtcgcc cacgacggcg ctggaaagag ggtctactac | 8750 |
| ctcacccgtg accctacaac ccccctcgcg agagctgcgt gggagacagc | 8800 |
| aagacacact ccagtcaatt cctggctagg caacataatc atgtttgccc | 8850 |
| ccacactgtg ggcgaggatg atactgatga cccattctt tagcgtcctt | 8900 |
| atagccaggg accagcttga acaggccctc gattgcgaga tctacggggc | 8950 |
| ctgctactcc atagaaccac ttgatctacc tccaatcatt caaagactcc | 9000 |
| atggcctcag cgcattttca ctccacagtt actctccagg tgaaattaat | 9050 |
| agggtggccg catgcctcag aaaacttggg gtaccgccct tgcgagcttg | 9100 |
| gagacaccgg gccggagcg tccgcgctag gcttctggcc agaggaggca | 9150 |
| gggctgccat atgtggcaag tacctcttca actgggcagt aagaacaaag | 9200 |
| ctcaaactca ctccaatagc ggccgctggc cagctggact tgtccggctg | 9250 |
| gttcacggct ggctacagcg ggggagacat ttatcacagc gtgtctcatg | 9300 |
| cccggccccg ctggatctgg ttttgcctac tcctgcttgc tgcagggta | 9350 |
| ggcatctacc tcctccccaa ccgatgaagg ttggggtaaa cactccggcc | 9400 |
| t | 9401 |

(2) INFORMATION FOR SEQ ID NO: 26:

(i) SEQUENCE CHARACTERISTICS:
        (A) LENGTH: 9416
        (B) TYPE: Nucleic
        (C) STRANDEDNESS: Single
        (D) TOPOLOGY: Linear (iv) ANTI-SENSE: NO (xi) SEQUENCE DESCRIPTION: SEQ ID NO: 26:

```
gccagccccc tgatgggggc gacactccac catgaatcac tccoctgtga         50
ggaactactg tcttcacgca gaaagcgtct agccatggcg ttagtatgag        100
tgtcgtgcag cctccaggac ccccctccc gggagagcca tagtggtctg         150
cggaaccggt gagtacaccg gaattgccag gacgaccggg tcctttcttg        200
gataaacccg ctcaatgcct ggagatttgg gcgtgccccc gcaagactgc        250
tagccgagta gtgttgggtc gcgaaaggcc ttgtggtact gcctgatagg        300
gtgcttgcga gtgccccggg aggtctcgta gaccgtgcac catgagcacg        350
aatcctaaac ctcaaagaaa aaccaaacgt aacaccaacc gtcgcccaca        400
ggacgtcaag ttcccgggtg gcggtcagat cgttggtgga gtttacttgt        450
tgccgcgcag gggccctaga ttgggtgtgc gcgcgacgag gaagacttcc        500
gagcggtcgc aacctcgagg tagacgtcag cctatcccca aggcacgtcg        550
gcccgagggc aggacctggg ctcagcccgg gtaccttgg cccctctatg         600
gcaatgaggg ttgcgggtgg gcgggatggc tcctgtctcc ccgtggctct        650
cggcctagct ggggccccac agacccccgg cgtaggtcgc gcaatttggg        700
taaggtcatc gataccctta cgtgcggctt cgccgacctc atggggtaca        750
taccgctcgt cggcgcccct cttggaggcg ctgccagggc cctggcgcat        800
ggcgtccggg ttctggaaga cggcgtgaac tatgcaacag gaaccttcc         850
tggttgctct ttctctatct tccttctggc cctgctctct tgcctgactg        900
tgcccgcttc agcctaccaa gtgcgcaatt cctcggggct ttaccatgtc        950
accaatgatt gccctaactc gagtgttgtg tacgaggcgc ccgatgccat       1000
cctgcacact ccggggtgtg tcccttgcgt tcgcgagggt aacgcctcga       1050
ggtgttgggt ggcggtgacc cccacggtgg ccaccaggga cggcaaactc       1100
cccacaacgc agcttcgacg tcatatcgat ctgcttgtcg ggagcgccac       1150
cctctgctcg gccctctacg tgggggacct gtgcgggtct gtctttcttg       1200
ttggtcaact gtttaccttc tctcccaggc accactggac gacgcaagac       1250
tgcaattgtt ctatctatcc cggccatata acgggtcatc gcatggcatg       1300
gaatatgatg atgaactggt cccctacggc agcgttggtg gtagctcagc       1350
tgctccgaat cccacaagcc atcatggaca tgatcgctgg cgcccactgg       1400
ggagtcctgg cggcataaa gtatttctcc atggtgggga actgggcgaa        1450
ggtcctggta gtgctgctgc tatttgccgg cgtcgacgcg gaaacccacg       1500
tcaccggggg aaatgccggc cgcaccacgg ctgggcttgt tggtctcctt       1550
acaccaggcg ccaagcagaa catccaactg atcaacacca acggcagttg       1600
gcacatcaat agcacggcct tgaactgcaa tgaaagcctt aacaccggct       1650
```

-continued

| | |
|---|---|
| ggttagcagg gctcttctat cagcacaaat tcaactcttc aggctgtcct | 1700 |
| gagaggttgg ccagctgccg acgccttacc gattttgccc agggctgggg | 1750 |
| tcctatcagt tatgccaacg gaagcggcct cgacgaacgc ccctactgct | 1800 |
| ggcactaccc tccaagacct tgtggcattg tcccgcaaa gagcgtgtgt | 1850 |
| ggcccggtat attgcttcac tcccagcccc gtggtggtgg gaacgaccga | 1900 |
| caggtcgggc gcgcctacct acagctgggg tgcaaatgat acggatgtct | 1950 |
| tcgtccttaa caacaccagg ccaccgctgg gcaattggtt cggttgtacc | 2000 |
| tggatgaact caactggatt caccaaagtg tgcggagcgc ccccttgtgt | 2050 |
| catcggaggg gtgggcaaca acaccttgct ctgccccact gattgcttcc | 2100 |
| gcaaatatcc ggaagccaca tactctcggt gcggctccgg tcccaggatt | 2150 |
| acacccaggt gcatggtcga ctaccgtat aggctttggc actatccttg | 2200 |
| taccatcaat tacaccatat tcaaagtcag gatgtacgtg ggaggggtcg | 2250 |
| agcacaggct ggaagcggcc tgcaactgga cgcggggcga acgctgtgat | 2300 |
| ctggaagaca gggacaggtc cgagctcagc ccgttgctgc tgtccaccac | 2350 |
| acagtggcag gtccttccgt gttctttcac gaccctgcca gccttgtcca | 2400 |
| ccggcctcat ccacctccac cagaacattg tggacgtgca gtacttgtac | 2450 |
| ggggtagggt caagcatcgc gtcctgggcc attaagtggg agtacgtcgt | 2500 |
| tctcctgttc cttctgcttg cagacgcgcg cgtctgttcc tgcttgtgga | 2550 |
| tgatgttact catatcccaa gcggaggcgg ctttggagaa cctcgtaata | 2600 |
| ctcaatgcag catccctggc cgggacgcat ggtcttgtgt ccttcctcgt | 2650 |
| gttcttctgc tttgcgtggt atctgaaggg taggtgggtg cccggagcgg | 2700 |
| tctacgcccc ctacgggatg tggcctctcc tcctgctcct gctggcgttg | 2750 |
| cctcagcggg catacgcact ggacacggag gtggccgcgt cgtgtggcgg | 2800 |
| cgttgttctt gtcgggttaa tggcgctgac tctgtcgcca tattacaagc | 2850 |
| gctatatcag ctggtgcatg tggtggcttc agtattttct gaccagagta | 2900 |
| gaagcgcaac tgcacgtgtg ggttcccccc ctcaacgtcc gggggggggcg | 2950 |
| cgatgccgtc atcttactca cgtgtgtagt acacccggcc ctggtatttg | 3000 |
| acatcaccaa actactcctg gccatcttcg gaccccttg gattcttcaa | 3050 |
| gccagtttgc ttaaagtccc ctacttcgtg cgcgttcaag gccttctccg | 3100 |
| gatctgcgcg ctagcgcgga agatagccgg aggtcattac gtgcaaatgg | 3150 |
| ccatcatcaa gttaggggcg cttactggca cctgtgtgta taaccatctc | 3200 |
| gctcctcttc gagactgggc gcacaacggc ctgcgagatc tggccgtggc | 3250 |
| tgtggaacca gtcgtcttct cccgaatgga gaccaagctc atcacgtggg | 3300 |
| gggcagatac cgccgcgtgc ggtgacatca tcaacggctt gccgtctct | 3350 |
| gcccgtaggg gccaggagat actgcttggg ccagccgacg gaatggtctc | 3400 |
| caagggtgg aggttgctgg cgcccatcac ggcgtacgcc cagcagacga | 3450 |
| gaggcctcct agggtgtata atcaccagcc tgactggccg ggacaaaaac | 3500 |
| caagtggagg gtgaggtcca gatcgtgtca actgctaccc agaccttcct | 3550 |
| ggcaacgtgc atcaatgggg tatgctggac tgtctaccac ggggccggaa | 3600 |
| cgaggaccat cgcatcaccc aagggtcctg tcatccagac gtataccaat | 3650 |

-continued

| | |
|---|---|
| gtggatcaag acctcgtggg ctggcccgct cctcaaggtt cccgctcatt | 3700 |
| gacaccctgc acctgcggct cctcggacct ttacctggtc acgaggcacg | 3750 |
| ccgatgtcat tcccgtgcgc cggcgaggtg atagcagggg tagcctgctt | 3800 |
| tcgcccggc ccatttccta cttgaaaggc tcctcggggg gtccgctgtt | 3850 |
| gtgccccacg ggacacgccg tgggcctatt cagggccgcg tgtgcaccc | 3900 |
| gtggagtggc taaggcggtg gactttatcc ctgtggagaa cctagagaca | 3950 |
| accatgagat ccccggtgtt cacggacaac tcctctccac cagcagtgcc | 4000 |
| ccagagcttc caggtggccc acctgcatgc tcccaccggc agcggtaaga | 4050 |
| gcaccaaggt cccggctgcg tacgcagcca agggctacaa ggtgttggtg | 4100 |
| ctcaaccct ctgttgctgc aacactgggc tttggtgctt acatgtccaa | 4150 |
| ggcccatggg gttgatccta atatcaggac cggggtgaga acaattacca | 4200 |
| ctggcagccc catcacgtac tccacctacg gcaagttcct tgccgacgcc | 4250 |
| gggtgctcag gaggtgctta tgacataata atttgtgacg agtgccactc | 4300 |
| cacggatgcc acatccatct cggcatcgg cactgtcctt gaccaagcag | 4350 |
| agactgcggg ggcgagactg gttgtgctcg ccactgctac ccctccgggc | 4400 |
| tccgtcactg tgtcccatcc taacatcgag gaggttgctc tgtccaccac | 4450 |
| cggagagatc cccttttacg gcaaggctat cccctcgag gtgatcaagg | 4500 |
| ggggaagaca tctcatcttc tgccactcaa agaagaagtg cgacgagctc | 4550 |
| gccgcgaagc tggtcgcatt gggcatcaat gccgtggcct actaccgcgg | 4600 |
| tcttgacgtg tctgtcatcc cgaccagcgg cgatgttgtc gtcgtgtcga | 4650 |
| ccgatgctct catgactggc tttaccggcg acttcgactc tgtgatagac | 4700 |
| tgcaacacgt gtgtcactca gacagtcgat tttagccttg accctacctt | 4750 |
| taccattgag acaaccacgc tcccccagga tgctgtctcc aggactcaac | 4800 |
| gccggggcag gactggcagg gggaagccag gcatctatag atttgtggca | 4850 |
| ccggggagc gcccctccgg catgttcgac tcgtccgtcc tctgtgagtg | 4900 |
| ctatgacgcg ggctgtgctt ggtatgagct cacgcccgcc gagactacag | 4950 |
| ttaggctacg agcgtacatg aacaccccgg ggcttcccgt gtgccaggac | 5000 |
| catcttggat tttgggaggg cgtctttacg ggcctcactc atatagatgc | 5050 |
| ccactttcta tcccagacaa agcagagtgg ggagaacttt ccttacctgg | 5100 |
| tagcgtacca agccaccgtg tgcgctaggg ctcaagcccc tccccccatcg | 5150 |
| tgggaccaga tgcggaagtg tttgatccgc cttaaaccca ccctccatgg | 5200 |
| gccaacaccc ctgctataca gactgggcgc tgttcagaat gaagtcaccc | 5250 |
| tgacgcaccc aatcaccaaa tacatcatga catgcatgtc ggccgacctg | 5300 |
| gaggtcgtca cgagcacctg ggtgctcgtt ggcggcgtcc tggctgctct | 5350 |
| ggccgcgtat tgcctgtcaa caggctgcgt ggtcatagtg ggcaggatcg | 5400 |
| tcttgtccgg gaagccggca attatacctg acagggaggt tctctaccag | 5450 |
| gagttcgatg agatggaaga gtgctctcag cacttaccgt acatcgagca | 5500 |
| agggatgatg ctcgctgagc agttcaagca gaaggccctc ggcctcctgc | 5550 |
| agaccgcgtc ccgccatgca gaggttatca cccctgctgt ccagaccaac | 5600 |

| | |
|---|---|
| tggcagaaac tcgaggtctt ttgggcgaag cacatgtgga atttcatcag | 5650 |
| tgggatacaa tacttggcgg gcctgtcaac gctgcctggt aaccccgcca | 5700 |
| ttgcttcatt gatggctttt acagctgccg tcaccagccc actaaccact | 5750 |
| ggccaaaccc tcctcttcaa catattgggg gggtgggtgg ctgcccagct | 5800 |
| cgccgccccc ggtgccgcta ccgccttgt ggcgctggc ttagctggcg | 5850 |
| ccgcactcga cagcgttgga ctggggaagg tcctcgtgga cattcttgca | 5900 |
| ggctatggcg cgggcgtggc gggagctctt gtggcattca agatcatgag | 5950 |
| cggtgaggtc ccctccacgg aggacctggt caatctgctg cccgccatcc | 6000 |
| tctcacctgg agcccttgca gtcggtgtgg tctttgcatc aatactgcgc | 6050 |
| cggcgtgttg gcccgggcga gggggcagtg caatggatga accggctaat | 6100 |
| agccttcgcc tcccggggga accatgtttc ccccacacac tacgtgccgg | 6150 |
| agagcgatgc agccgcccgc gtcactgcca tactcagcag cctcactgta | 6200 |
| acccagctcc tgaggcgact gcatcagtgg ataagctcgg agtgtaccac | 6250 |
| tccatgctcc ggttcctggc taagggacat ctgggactgg atatgcgagg | 6300 |
| tgctgagcga ctttaagacc tggctgaaag ccaagctcat gccacaactg | 6350 |
| cctgggattc cctttgtgtc ctgccagcgc gggtataggg gggtctggcg | 6400 |
| aggagacggc attatgcaca ctcgctgcca ctgtggagct gagatcactg | 6450 |
| gacatgtcaa aaacgggacg atgaggatcg tcggtcctag gacctgcaag | 6500 |
| aacatgtgga gtgggacgtt cttcattaat gcctacacca cgggcccctg | 6550 |
| tactccccctt cctgcgccga actataagtt cgcgctgtgg agggtgtctg | 6600 |
| cagaggaata cgtggagata aggcgggtgg gggacttcca ctacgtatcg | 6650 |
| ggcatgacta ctgacaatct caaatgcccg tgccagatcc catcgcccga | 6700 |
| attttttcaca gaattggacg gggtgcgcct acataggttt gcgccccctt | 6750 |
| gcaagccctt gctgcgggag gaggtatcat tcagagtagg actccacgag | 6800 |
| tacccggtgg ggtcgcaatt accttgcgag cccgaaccgg acgtagccgt | 6850 |
| gttgacgtcc atgctcactg atccctccca tataacagca gaggcggccg | 6900 |
| ggagaaggtt ggcgagaggg tcacccccctt ctatggccag ctcctcggct | 6950 |
| agccagctgt ccgctccatc tctcaaggca acttgcaccg ccaaccatga | 7000 |
| ctcccctgac gccgagctca tagaggctaa cctcctgtgg aggcaggaga | 7050 |
| tgggcggcaa catcaccagg gttgagtcag agaacaaagt ggtgattctg | 7100 |
| gactccttcg atccgcttgt ggcagaggag gatgagcggg aggtctccgt | 7150 |
| acccgcagaa attctgcgga agtctcggag attcgcccca gccctgcccg | 7200 |
| tctgggcgcg gccggactac aaccccctgc tagtagagac gtggaaaaag | 7250 |
| cctgactacg aaccacctgt ggtccatggc tgccgctac cacctccacg | 7300 |
| gtcccctcct gtgcctccgc ctcggaaaaa gcgtacggtg gtcctcaccg | 7350 |
| aatcaaccct acctactgcc ttggccgagc ttgccaccaa aagttttggc | 7400 |
| agctcctcaa cttccggcat tacgggcgac aatacgacaa catcctctga | 7450 |
| gcccgcccct tctggctgcc ccccgactc cgacgttgag tcctattctt | 7500 |
| ccatgccccc cctggagggg gagcctgggg atccggatct cagcgacggg | 7550 |
| tcatggtcga cggtcagtag tggggccgac acggaagatg tcgtgtgctg | 7600 |

```
ctcaatgtct tattcctgga caggcgcact cgtcaccccg tgcgctgcgg        7650
aggaacaaaa actgcccatc aacgcactga gcaactcgtt gctacgccat        7700
cacaatctgg tgtattccac cacttcacgc agtgcttgcc aaaggaagaa        7750
gaaagtcaca tttgacagac tgcaagttct ggacagccat taccaggacg        7800
tgctcaagga ggtcaaagca gcggcgtcaa aagtgaaggc taacttgcta        7850
tccgtagagg aagcttgcag cctggcgccc ccacattcag ccaaatccaa        7900
gtttggctat ggggcaaaag acgtccgttg ccatgccaga aaggccgtag        7950
cccacatcaa ctccgtgtgg aaagaccttc tggaagacag tgtaacacca        8000
atagacacta ccatcatggc caagaacgag gttttctgcg ttcagcctga        8050
gaagggggt cgtaagccag ctcgtctcat cgtgttcccc gacctgggcg         8100
tgcgcgtgtg cgagaagatg gccctgtacg acgtggttag caagctcccc        8150
ttggccgtga tgggaagctc ctacggattc caatactcac caggacagcg        8200
ggttgaattc ctcgtgcaag cgtggaagtc caagaagacc ccgatggggc        8250
tctcgtatga tacccgctgt tttgactcca cagtcactga gagcgacatc        8300
cgtacggagg aggcaattta ccaatgttgt gacctggacc cccaagcccg        8350
cgtggccatc aagtccctca ctgagaggct ttatgttggg ggccctctta        8400
ctaattcaag gggggaaaac tgcggctacc gcaggtgccg cgcgagcaga        8450
gtactgacaa ctagctgtgg taacaccctc actcgctaca tcaaggcccg        8500
ggcagcctgt cgagccgcag ggctccagga ctgcaccatg ctcgtgtgtg        8550
gcgacgactt agtcgttatc tgtgaaagtg cgggggtcca ggaggacgcg        8600
gcgagcctga gagccttcac ggaggctatg accaggtact ccgccccccc        8650
cggggacccc ccacaaccag aatacgactt ggagcttata acatcatgct        8700
cctccaacgt gtcagtcgcc cacgacggcg ctggaaagag ggtctactac        8750
cttacccgtg accctacaac ccccctcgcg agagccgcgt gggagacagc        8800
aagacacact ccagtcaatt cctggctagg caacataatc atgtttgccc        8850
ccacactgtg ggcgaggatg atactgatga cccacttctt tagcgtcctc        8900
atagccaggg atcagcttga acaggctctc aactgcgaga tctacggagc        8950
ctgctactcc atagaaccac tggatctacc tccaatcatt caaagactcc        9000
atggcctcag cgcattttca ctccacagtt actctccagg tgaaattaat        9050
agggtggccg catgcctcag aaaacttggg gtcccgccct tgcgagcttg        9100
gagacaccgg gcctggagcg tccgcgctag gcttctggcc agaggaggca        9150
aggctgccat atgtggcaag tacctcttca actgggcagt aagaacaaag        9200
ctcaaactca ctccgataac ggccgctggc cggctggact tgtccggctg        9250
gttcacggct ggctacagcg ggggagacat ttatcacagc gtgtctcatg        9300
cccggccccg ctggttctgg ttttgcctac tcctgcttgc tgcagggta         9350
ggcatctacc tcctccccaa ccgatgaaga ttgggctaac cactccaggc        9400
caataggcca ttccct                                             9416
```

(2) INFORMATION FOR SEQ ID NO: 27:

(i) SEQUENCE CHARACTERISTICS:
     (A) LENGTH: 9416

(B) TYPE: Nucleic
(C) STRANDEDNESS: Single
(D) TOPOLOGY: Linear (iv) ANTI-SENSE: NO (xi) SEQUENCE DESCRIPTION: SEQ ID NO: 27:

| | | |
|---|---|---|
| cgattggggg cgacactcca ccatagatca ctcccctgtg aggaactact | 50 |
| gtcttcacgc agaaagcgtc tagccatggc gttagtatga gtgtcgtgca | 100 |
| gcctccagga cccccctcc cgggagagcc atagtggtct gcggaaccgg | 150 |
| tgagtacacc ggaattgcca ggacgaccgg gtcctttctt ggatcaaccc | 200 |
| gctcaatgcc tggagatttg ggcgtgcccc cgcgagactg ctagccgagt | 250 |
| agtgttgggt cgcgaaaggc cttgtggtac tgcctgatag ggtgcttgcg | 300 |
| agtgccccgg gaggtctcgt agaccgtgca ccatgagcac gaatcctaaa | 350 |
| cctcaaagaa aaccaaacg taacaccaac cgccgcccac aggacgtcaa | 400 |
| gttcccgggc ggtggtcaga tcgttggtgg agtttacctg ttgccgcgca | 450 |
| ggggccccag gttgggtgtg cgcgcgccca ggaagacttc cgagcggtcg | 500 |
| caacctcgtg gaaggcgaca acctatcccc aaggctcgcc ggcccgaggg | 550 |
| caggacctgg gctcagcccg ggtacccttg gcctctctat ggcaatgagg | 600 |
| gcttaggggtg ggcaggatgg ctcctgtcac cccgcggctc ccggcctagt | 650 |
| tggggcccca cggaccccg gcgtaggtcg cgtaatttgg gtaaggtcat | 700 |
| cgataccctc acatgcggct tcgccgatct catgggggtac attccgctcg | 750 |
| tcggcgcccc cctgggggc gctgccaggg ccctggcaca tggtgtccgg | 800 |
| gttctggagg acggcgtgaa ctatgcaaca gggaatctgc ccggttgctc | 850 |
| tttttctatc ttcctcttgg ctctgctgtc ctgcctgacc accccagctt | 900 |
| ccgcttacga agtgcacaac gtgtccggga tatatcatgt cacgaacgac | 950 |
| tgctccaacg caagcattgt gtatgaggca gcggacttga tcatgcatac | 1000 |
| tcctgggtgc gtgccctgcg ttcgggaagg caactcctcc cgctgctggg | 1050 |
| tagcgctcac tccacgctc gcagccagga acgtcaccat ccccaccacg | 1100 |
| acgatacgac gccacgtcga tctgctcgtt ggggcggctg cttttctgttc | 1150 |
| cgctatgtac gtgggggacc tctgcggatc tgttttcctc gtctctcagc | 1200 |
| tgttcacctt ctcgcctcgc cggcatgtga cattacagga ctgtaactgc | 1250 |
| tcaatttatc ccggccatgt gtcgggtcac cgtatggctt gggacatgat | 1300 |
| gatgaactgg tcgcccacaa cagccctagt ggtgtcgcag ttactccgga | 1350 |
| tcccacaagc cgtcgtggac atggtggcgg ggcccactg gggagtcctg | 1400 |
| gcgggccttg cctactattc catggcgggg aactgggcta aggttctgat | 1450 |
| tgtgatgcta cttttttgctg gcgttgacgg ggatacccac gtgacagggg | 1500 |
| gggcgcaagc caaaaccacc aacaggctcg tgtccatgtt cgcaagtggg | 1550 |
| ccgtctcaga aaatccagct tataaacacc aatgggagtt ggcacatcaa | 1600 |
| caggactgcc ctgaactgca atgactctct ccagactggg tttcttgccg | 1650 |
| cgctgttcta cacacatagt ttcaactcgt ccgggtgccc agagcgcatg | 1700 |
| gcccagtgcc gcaccattga caagttcgac cagggatggg gtcccattac | 1750 |
| ttatgctgag tctagcagat cagaccagag gccatattgc tggcactacc | 1800 |

-continued

| | |
|---|---|
| cacctccaca atgtaccatc gtacctgcgt cggaggtgtg cggcccagtg | 1850 |
| tactgcttca ccccaagccc tgtcgtcgtg gggacgaccg atcgtttcgg | 1900 |
| tgtccctacg tatagatggg gggagaacga gactgacgtg ctgctgctca | 1950 |
| acaacacgcg gccgccgcaa ggcaactggt tcggctgcac atggatgaat | 2000 |
| agcaccgggt tcaccaagac atgtgggggg cccccgtgta acatcggggg | 2050 |
| ggtcggcaac aacaccctga cctgccccac ggactgcttc cggaagcacc | 2100 |
| ccgaggctac ctacacaaaa tgtggttcgg ggccttggct gacacctagg | 2150 |
| tgcatggttg actatccata caggctctgg cattacccct gcactgttaa | 2200 |
| ctttaccatc ttcaaggtta ggatgtatgt ggggggggtg gagcacaggc | 2250 |
| tcaatgctgc atgcaattgg acccgaggag agcgttgtga cttggaggac | 2300 |
| agggataggc cggagctcag cccgctgctg ctgtctacaa cagagtggca | 2350 |
| ggtactgccc tgttccttca ccaccctacc agctctgtcc actggcttga | 2400 |
| ttcacctcca tcagaacatc gtggacgtgc aatacctata cggtataggg | 2450 |
| tcagcggttg tctcctttgc aatcaaatgg gagtatgtcc tgttgctttt | 2500 |
| ccttctccta gcggacgcac gtgtctgtgc ctgcttgtgg atgatgctgc | 2550 |
| tgatagccca ggccgaggcc gccttggaga acctggtggt cctcaattcg | 2600 |
| gcgtctgtgg ccgcgcaca tggcatcctc tccttccttg tgttcttctg | 2650 |
| tgccgcctgg tacatcaaag gcaggctggt ccctggggcg acatatgctc | 2700 |
| tttatggcgt gtggccgctg ctcctgctct tgctggcatt accaccgcga | 2750 |
| gcttacgcca tggaccggga gatggctgca tcgtgcggag gcgcggtttt | 2800 |
| tgtgggtctg gtactcctga ctttgtcacc atactacaag gtgttcctcg | 2850 |
| ctaggctcat atggtggtta caatatttta ccaccagagc cgaggcggac | 2900 |
| ttacatgtgt ggatccccc cctcaacgct cggggaggcc gcgatgccat | 2950 |
| catcctcctc atgtgcgcag tccatccaga gctaatcttt gacatcacca | 3000 |
| aacttctaat tgccatactc ggtccgctca tggtgctcca agctggcata | 3050 |
| accagagtgc cgtacttcgt gcgcgctcaa gggctcattc atgcatgcat | 3100 |
| gttagtgcgg aaggtcgctg ggggtcatta tgtccaaatg gccttcatga | 3150 |
| agctgggcgc gctgacaggc acgtacattt acaaccatct taccccgcta | 3200 |
| cgggattggc cacgcgcggg cctacgagac cttgcggtgg cagtggagcc | 3250 |
| cgtcgtcttc tccgacatgg agaccaagat catcacctgg ggagcagaca | 3300 |
| ccgcggcgtg tggggacatc atcttgggtc tgcccgtctc cgcccgaagg | 3350 |
| ggaaaggaga tactcctggg cccggccgat agtcttgaag ggcgggggtt | 3400 |
| gcgactcctc gcgcccatca cggcctactc ccaacagacg cggggcctac | 3450 |
| ttggttgcat catcactagc cttacaggcc gggacaagaa ccaggtcgag | 3500 |
| ggagaggttc aggtggtttc caccgcaaca caatccttcc tggcgacctg | 3550 |
| cgtcaacggc gtgtgttgga ccgtttacca tggtgctggc tcaaagacct | 3600 |
| tagccgcgcc aaaggggcca atcacccaga tgtacactaa tgtggaccag | 3650 |
| gacctcgtcg gctgcccaa gcccccgggg gcgcgttcct tgacaccatg | 3700 |
| cacctgtggc agctcagacc tttacttggt cacgagacat gctgacgtca | 3750 |

-continued

| | |
|---|---|
| ttccggtgcg ccggcggggc gacagtaggg ggagcctgct ctcccccagg | 3800 |
| cctgtctcct acttgaaggg ctcttcgggt ggtccactgc tctgcccctt | 3850 |
| cgggcacgct gtgggcatct tccgggctgc cgtatgcacc cgggggggttg | 3900 |
| cgaaggcggt ggactttgtg cccgtagagt ccatggaaac tactatgcgg | 3950 |
| tctccggtct tcacggacaa ctcatccccc cggccgtac cgcagtcatt | 4000 |
| tcaagtggcc cacctacacg ctcccactgg cagcggcaag agtactaaag | 4050 |
| tgccggctgc atatgcagcc caagggtaca aggtgctcgt cctcaatccg | 4100 |
| tccgttgccg ctaccttagg gtttggggcg tatatgtcta aggcacacgg | 4150 |
| tattgacccc aacatcagaa ctggggtaag gaccattacc acaggcgccc | 4200 |
| ccgtcacata ctctacctat ggcaagtttc ttgccgatgg tggttgctct | 4250 |
| gggggcgctt atgacatcat aatatgtgat gagtgccatt caactgactc | 4300 |
| gactacaatc ttgggcatcg gcacagtcct ggaccaagcg gagacggctg | 4350 |
| gagcgcggct tgtcgtgctc gccaccgcta cgcctccggg atcggtcacc | 4400 |
| gtgccacacc caaacatcga ggaggtggcc ctgtctaata ctggagagat | 4450 |
| ccccttctat ggcaaagcca tcccattga agccatcagg gggggaaggc | 4500 |
| atctcatttt ctgtcattcc aagaagaagt gcgacgagct cgccgcaaag | 4550 |
| ctgtcaggcc tcggaatcaa cgctgtggcg tattaccggg ggctcgatgt | 4600 |
| gtccgtcata ccaactatcg gagacgtcgt tgtcgtggca acagacgctc | 4650 |
| tgatgacggg ctatacgggc gactttgact cagtgatcga ctgtaacaca | 4700 |
| tgtgtcaccc agacagtcga cttcagcttg gatcccacct tcaccattga | 4750 |
| gacgacgacc gtgcctcaag acgcagtgtc gcgctcgcag cggcggggta | 4800 |
| ggactggcag gggtaggaga ggcatctaca ggtttgtgac tccggagaa | 4850 |
| cggccctcgg gcatgttcga ttcctcggtc ctgtgtgagt gctatgacgc | 4900 |
| gggctgtgct tggtacgagc tcaccccggc cgagacctcg gttaggttgc | 4950 |
| gggcctacct gaacacacca gggttgcccg tttgccagga ccacctggag | 5000 |
| ttctgggaga gtgtcttcac aggcctcacc catatagatg cacacttctt | 5050 |
| gtcccagacc aagcaggcag gagacaactt cccctacctg gtagcatacc | 5100 |
| aagccacggt gtgcgccagg gctcaggccc cacctccatc atgggatcaa | 5150 |
| atgtggaagt gtctcatacg gctgaaacct acgctgcacg ggccaacacc | 5200 |
| cttgctgtac aggctgggag ccgtccagaa tgaggtcacc ctcacccacc | 5250 |
| ccataaccaa atacatcatg gcatgcatgt cggctgacct ggaggtcgtc | 5300 |
| actagcacct gggtgctggt gggcggagtc cttgcagctc tggccgcgta | 5350 |
| ttgcctgaca acaggcagtg tggtcattgt gggtaggatt atcttgtccg | 5400 |
| ggaggccggc cattgttccc gacagggagc ttctctacca ggagttcgat | 5450 |
| gaaatggaag agtgcgcctc gcacctccct tacatcgagc agggaatgca | 5500 |
| gctcgccgag caattcaagc agaaagcgct cgggttactg caaacagcca | 5550 |
| ccaaacaagc ggaggctgct gctcccgtgg tggagtccaa gtggcgagcc | 5600 |
| cttgagacat tctgggcgaa gcacatgtgg aatttcatca gcgggataca | 5650 |
| gtacttagca ggcttatcca ctctgcctgg gaaccccgca atagcatcat | 5700 |
| tgatggcatt cacagcctct atcaccagcc cgctcaccac ccaaagtacc | 5750 |

| | |
|---|---|
| ctcctgttta acatcttggg ggggtggtg gctgcccaac tcgcccccc | 5800 |
| cagcgccgct tcggctttcg tgggcgccgg catcgccggt gcggctgttg | 5850 |
| gcagcatagg ccttgggaag gtgcttgtgg acattctggc gggttatgga | 5900 |
| gcaggagtgg ccggcgcgct cgtggccttt aaggtcatga gcggcgagat | 5950 |
| gccctccacc gaggacctgg tcaatctact tcctgccatc ctctctcctg | 6000 |
| gcgccctggt cgtcggggtc gtgtgtgcag caatactgcg tcgacacgtg | 6050 |
| ggtccgggag aggggggctgt gcagtggatg aaccggctga tagcgttcgc | 6100 |
| ctcgcggggt aatcatgttt cccccacgca ctatgtgcct gagagcgacg | 6150 |
| ccgcagcgcg tgttactcag atcctctcca gccttaccat cactcagctg | 6200 |
| ctgaaaaggc tccaccagtg gattaatgaa gactgctcca caccgtgttc | 6250 |
| cggctcgtgg ctaagggatg tttgggactg atatgcacg gtgttgactg | 6300 |
| acttcaagac ctggctccag tccaagctcc tgccgcagct acctggagtc | 6350 |
| cctttttctct cgtgccaacg cgggtacaag ggagtctggc ggggagacgg | 6400 |
| catcatgcaa accacctgcc catgtggagc acagatcacc ggacatgtca | 6450 |
| aaaacggttc catgaggatc gtcgggccta agacctgcag caaacgtgg | 6500 |
| catggaacat tccccatcaa cgcatacacc acgggcccct gcacaccctc | 6550 |
| tccagcgcca aactattcta gggcgctgtg gcgggtggcc gctgaggagt | 6600 |
| acgtggaggt cacgcgggtg ggggatttcc actacgtgac gggcatgacc | 6650 |
| actgacaacg taaagtgccc atgccaggtt ccggctcctg aattcttctc | 6700 |
| ggaggtggac ggagtgcggt tgcacaggta cgctccggcg tgcaggcctc | 6750 |
| tcctacggga ggaggttaca ttccaggtcg ggctcaacca atacctggtt | 6800 |
| gggtcacagc taccatgcga gcccgaaccg gatgtagcag tgctcacttc | 6850 |
| catgctcacc gacccctccc acatcacagc agaaacggct aagcgtaggt | 6900 |
| tggccagggg gtctcccccc tccttggcca gctcttcagc tagccagttg | 6950 |
| tctgcgcctt ccttgaaggc gacatgcact acccaccatg tctctccgga | 7000 |
| cgctgacctc atcgaggcca acctcctgtg gcggcaggag atgggcggga | 7050 |
| acatcacccg cgtggagtcg gagaacaagg tggtagtcct ggactctttc | 7100 |
| gacccgcttc gagcggagga ggatgagagg gaagtatccg ttccggcgga | 7150 |
| gatcctgcgg aaatccaaga agttccccgc agcgatgccc atctgggcgc | 7200 |
| gcccggatta caaccctcca ctgttagagt cctggaagga cccggactac | 7250 |
| gtccctccgg tggtgcacgg gtgcccgttg ccacctatca aggcccctcc | 7300 |
| aataccacct ccacgagaa agaggacggt tgtcctaaca gagtcctccg | 7350 |
| tgtcttctgc cttagcggag ctcgctacta agaccttcgg cagctccgaa | 7400 |
| tcatcggcc tcgacagcgg cacggcgacc gcccttcctg accaggcctc | 7450 |
| cgacgacggt gacaaaggat ccgacgttga gtcgtactcc tccatgcccc | 7500 |
| cccttgaggg ggaaccgggg gaccccgatc tcagtgacgg gtcttggtct | 7550 |
| accgtgagcg aggaagctag tgaggatgtc gtctgctgct caatgtccta | 7600 |
| cacatggaca ggcgccttga tcacgccatg cgctgcggag gaaagcaagc | 7650 |
| tgcccatcaa cgcgttgagc aactctttgc tgcgccacca taacatggtt | 7700 |

-continued

```
tatgccacaa catctcgcag cgcaggcctg cggcagaaga aggtcacctt    7750
tgacagactg caagtcctgg acgaccacta ccgggacgtg ctcaaggaga    7800
tgaaggcgaa ggcgtccaca gttaaggcta aactcctatc cgtagaggaa    7850
gcctgcaagc tgacgccccc acattcggcc aaatccaagt ttggctatgg    7900
ggcaaaggac gtccggaacc tatccagcaa ggccgttaac cacatccact    7950
ccgtgtggaa ggacttgctg aagacactg tgacaccaat tgacaccacc     8000
atcatggcaa aaaatgaggt tttctgtgtc caaccagaga aaggaggccg    8050
taagccagcc cgccttatcg tattcccaga tctgggagtc cgtgtatgcg    8100
agaagatggc cctctatgat gtggtctcca cccttcctca ggtcgtgatg    8150
ggctcctcat acggattcca gtactctcct gggcagcgag tcgagttcct    8200
ggtgaatacc tggaaatcaa agaaaaaccc catgggcttt tcatatgaca    8250
ctcgctgttt cgactcaacg gtcaccgaga acgacatccg tgttgaggag    8300
tcaatttacc aatgttgtga cttggccccc gaagccagac aggccataaa    8350
atcgctcaca gagcggcttt atatcggggg tcctctgact aattcaaaag    8400
ggcagaactg cggttatcgc cggtgccgcg cgagcggcgt gctgacgact    8450
agctgcggta acaccctcac atgttacttg aaggcctctg cagcctgtcg    8500
agctgcgaag ctccaggact gcacgatgct cgtgaacgga gacgacctcg    8550
tcgttatctg tgaaagcgcg ggaacccaag aggacgcggc gagcctacga    8600
gtcttcacgg aggctatgac taggtactcc gccccccccg gggacccgcc    8650
ccaaccagaa tacgacttgg agctgataac atcatgttcc tccaatgtgt    8700
cggtcgccca cgatgcatca ggcaaaaggg tgtactacct cacccgtgat    8750
cccaccaccc ccctagcacg ggctgcgtgg gagacagcta gacacactcc    8800
agttaactcc tggctaggca acattattat gtatgcgccc actttgtggg    8850
caaggatgat tctgatgact cacttcttct ccatccttct agcgcaggag    8900
caacttgaaa aagccctgga ctgccagatc tacggggcct gttactccat    8950
tgagccactt gacctacctc agatcattga acgactccat ggccttagcg    9000
cattttcact ccatagttac tctccaggtg agatcaatag ggtggcttca    9050
tgcctcagga aacttggggt accacccttg cgagtctgga gacatcgggc    9100
caggagcgtc cgcgctaggc tactgtccca gggagggagg gccgccactt    9150
gtggcaaata cctcttcaac tgggcagtaa aaaccaaact taaactcact    9200
ccaatcccgg ctgcgtcccg gctggacttg tccggctggt tcgttgctgg    9250
ttacagcggg ggagacatat atcacagcct gtctcgtgcc cgaccccgtt    9300
ggttcatgct gtgcctactc ctactttctg taggggtagg catctacctg    9350
ctccccaacc gatgaacggg gagataaaca ctccaggcca ataggccatc    9400
ccccttttt ttttt                                          9416
```

COMPOSITIONS AND METHODS FOR TREATMENT OF HEPATITIS C VIRUS ASSOCIATED DISEASES

This is a continuation of application Ser. No. 08/453,085, filed May 30, 1995, now abandoned which is a continuation of application Ser. No. 07/945,289, filed Sep. 10, 1972, now abandoned.

FIELD OF THE INVENTION

This invention relates to the design and synthesis of antisense oligonucleotides which can be administered to inhibit the replication of Hepatitis C virus in vivo or in vitro and to treat Hepatitis C virus-associated disease. These compounds can be used either prophylactically or therapeutically to reduce the severity of diseases associated with Hepatitis C virus. Oligonucleotides which are specifically hybridizable with RNA targets are disclosed.

BACKGROUND OF THE INVENTION

The predominant form of hepatitis currently resulting from transfusions is not related to the previously characterized Hepatitis A virus or Hepatitis B virus and has been referred to as Non-A, Non-B Hepatitis (NANBH). NANBH currently accounts for over 90% of cases of post-transfusion hepatitis. Estimates of the frequency of NANBH in transfusion recipients range from 5%–13% for those receiving volunteer blood, or 25–54% for those receiving blood from commercial sources.

Acute NANBH, while often less severe than acute disease caused by Hepatitis A or Hepatitis B viruses, occasionally leads to severe or fulminant hepatitis. Of greater concern, progression to chronic hepatitis is much more common after NANBH than after either Hepatitis A or Hepatitis B infection. Chronic NANBH has been reported in 10%–70% of infected individuals. This form of hepatitis can be transmitted even by asymptomatic patients, and frequently progresses to malignant disease such as cirrhosis and hepatocellular carcinoma. Chronic active hepatitis, with or without cirrhosis, is seen in 44%–90% of posttransfusion hepatitis cases. Of those patients who developed cirrhosis, approximately one-fourth died of liver failure.

Chronic active NANBH is a significant problem to hemophiliacs who are dependent on blood products; 5%–11% of hemophiliacs die of chronic end-stage liver disease. Cases of NANBH other than those traceable to blood or blood products are frequently associated with hospital exposure, accidental needle stick, or tattooing. Transmission through close personal contact also occurs, though this is less common for NANBH than for Hepatitis B.

The causative agent of the majority of NANBH has recently been identified and is now referred to as Hepatitis C Virus (HCV). Houghton et al., EP Publication 318,216; Choo et al., Science 1989, 244, 359–362. Based on serological studies using recombinant DNA-generated antigens it is now clear that HCV is the causative agent of most cases of post-transfusion NANBH. Clones of cDNA prepared from nucleic acid isolated from concentrated virus particles were originally isolated based on their ability to encode polypeptides which reacted with sera from NANBH patients. These clones hybridized with RNA, but not DNA, isolated from infected liver tissue, indicating the presence of an RNA genome. Hybridization analyses and sequencing of the cDNA clones revealed that RNA present in infected liver and particles was the same polarity as that of the coding strand of the cDNAs; in other words, the virus genome is a positive or plus-strand RNA genome. EP Publication 318, 216 (Houghton et al.) disclose partial genomic sequences of HCV-1, and teach recombinant DNA methods of cloning and expressing HCV sequences and HCV polypeptides, techniques of HCV immunodiagnostics, HCV probe diagnostic techniques, anti-HCV antibodies, and methods of isolating new HCV sequences. Houghton et al. also disclose additional HCV sequences and teach application of these sequences and polypeptides in immunodiagnostics, probe diagnostics, anti-HCV antibody production, PCR technology and recombinant DNA technology. The concept of using antisense polynucleotides as inhibitors of viral replication is disclosed, but no specific targets are taught. Oligomer probes and primers based on the sequences disclosed are also provided. EP Publication 419,182 (Miyamura et al.) discloses new HCV isolates J1 and J7 and use of sequences distinct from HCV-1 sequences for screens and diagnostics.

The only treatment regimen shown to be effective for the treatment of chronic NANBH is interferon-$\alpha$. Most NANBH patients show an improvement of clinical symptoms during interferon treatment, but relapse is observed in at least half of patients when treatment is interrupted. Significant improvements in antiviral therapy are therefore greatly desired.

OBJECTS OF THE INVENTION

It is an object of this invention to provide oligonucleotides which are capable of hybridizing with RNA of HCV to inhibit the synthesis or function of said RNA.

It is another object of this invention to provide oligonucleotides which are capable of hybridizing with RNA of HCV to inhibit replication of the virus.

It is a further object to provide oligonucleotides which can modulate the expression of HCV through antisense interaction with viral RNA.

Yet another object of this invention is to provide methods of prophylaxis, diagnostics and therapeutics for acute or chronic HCV infection.

A further object of this invention is to provide methods of prophylaxis, diagnostics and therapeutics for HCV-associated diseases.

Methods, materials and kits for detecting the presence or absence of HCV or HCV RNA in a sample suspected of containing it are further objects of the invention.

These and other objects will become apparent to persons of ordinary skill in the art from a review of the instant specification and appended claims.

SUMMARY OF THE INVENTION

In accordance with the present invention, compositions and methods for modulating the effects of HCV infection are provided. Oligonucleotides complementary to, and specifically hybridizable with, selected sequences of HCV RNA are provided. The HCV 5' end hairpin loop, 5' end 6-base-pair repeats, 5' end untranslated region, polyprotein translation initiation codon, ORF 3 translation initiation codon, 3'-untranslated region, 3' end palindrome region, R2 sequence and 3' end hairpin loop are preferred targets. Methods for diagnosing or treating disease states by administering oligonucleotides, either alone or in combination with a pharmaceutically acceptable carrier, to animals suspected of having HCV-associated diseases are also provided.

The relationship between the target RNA and oligonucleotides complementary to at least a portion of the target, and specifically hybridizable with it, is commonly denoted as "antisense". The oligonucleotides are able to inhibit the function of viral RNA by interfering with its replication, transcription into mRNA, translation into protein, packaging into viral particles or any other activity necessary to its overall biological function. The failure of the RNA to perform all or part of its function results in failure of all or a portion of the normal life cycle of the virus.

It has been found that antisense oligonucleotides designed to target viruses can be effective in diminishing viral infection. It is preferred that oligonucleotides have between about 5 and about 50 nucleotide units. It is also preferred that the oligonucleotides be specifically hybridizable with the HCV 5' end hairpin loop, 5' end 6-base-pair repeats, 5' end untranslated region, polyprotein translation initiation codon, ORF 3 translation initiation codon, 3'-untranslated region, 3' end palindrome region, R2 sequence or 3' end hairpin loop. The oligonucleotide may be modified to increase nuclease resistance and to increase its efficacy.

In accordance with preferred embodiments, the viral RNA is interfered with to an extent sufficient to inhibit HCV infection and/or HCV replication. Thus, oligonucleotides which are capable of interacting with portions of HCV RNA are comprehended. Animals suspected of having HCV-associated disease are contacted with an oligonucleotide made in accordance with this invention. In particular, the present invention is believed to be effective in the treatment of acute and chronic HCV infections and HCV-associated disease, either prophylactically or therapeutically.

It is to be expected that differences in the RNA of HCV from different strains and from different types within a strain exist. Thus, it is believed, for example, that the regions of the various HCV strains serve essentially the same function for the respective strains and that interference with expression of the genetic information will afford similar results in the various strains. This is believed to be so even though differences in the nucleotide sequences among the strains exist.

Accordingly, nucleotide sequences set forth in the present specification will be understood to be representational for the particular strain being described. Homologous or analogous sequences for different strains of HCV are specifically contemplated as being within the scope of this invention.

DETAILED DESCRIPTION OF PREFERRED EMBODIMENTS

Antisense oligonucleotides hold great promise as therapeutic agents for the treatment of many human diseases. In most cases, oligonucleotides complementary to specific RNA target sequences bind by Watson-Crick base pairing to pre-mRNA or mature mRNA, inhibiting the flow of genetic information from DNA to protein. In the case of RNA viruses such as HCV, oligonucleotides are designed to specifically hybridize to viral genomic RNA, mRNA, or replicative intermediate RNA, interfering with the function of the RNA such that viral replication or protein expression is modulated.

Numerous recent studies have documented the utility of antisense oligonucleotides as biochemical tools for studying target proteins. Rothenberg et al., *J. Natl. Cancer Inst.* 1989, 81, 1539–1544; Zon, G. *Pharmaceutical Res.* 1987, 5, 539–549. Because of recent advances in oligonucleotide chemistry, synthesis of nuclease-resistant oligonucleotides, and availability of types of oligonucleotides which exhibit enhanced cell uptake, it is now possible to consider the use of antisense oligonucleotides as a novel form of therapeutics.

For therapeutics, an animal suspected of having an HCV infection or HCV-associated disease is treated by administering oligonucleotides in accordance with this invention. Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as, for example, antimicrobial agents, antiinflammatory agents, anesthetics, and the like in addition to oligonucleotide.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Dosage and frequency will vary depending on, for example, body weight of patient and means of administration. Individual doses will normally range from about 0.001 mg to 500 mg, but may be higher or lower. Persons of ordinary skill can easily determine optimum dosages, dosing methodologies and repetition rates.

The present invention employs oligonucleotides complementary to specific regions of HCV. RNA for antisense inhibition of HCV. In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of some preferred oligonucleotides envisioned for this invention may contain phosphorothioates, phosphotriesters, methyl phosphonates, chain alkyl or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures. Summerton, J. E. and Weller, D. D. U.S. Pat. No.

5,034,506. In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 1991, 254, 1497. Other preferred oligonucleotides may contain alkyl and halogen-substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group.

All such oligonucleotides are comprehended by this invention so long as they function effectively to hybridize with HCV RNA. The oligonucleotides in accordance with this invention preferably comprise from about 5 to about 50 nucleic acid base units. It is more preferred that such oligonucleotides comprise from about 8 to 30 nucleic acid base units, and still more preferred to have from about 12 to 25 nucleic acid base units. As will be appreciated, a nucleic acid base unit is a base-sugar combination suitably bound to adjacent nucleic acid base unit through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides are well within the talents of the routineer. It is also well known to use similar techniques to prepare other oligonucleotides such as the phosphorothioates and alkylated derivatives.

In accordance with this invention, persons of ordinary skill in the art will understand that messenger RNA includes not only the sequence information to encode a protein using the three letter genetic code, but also associated ribonucleotides which form regions known to such persons as the 5'-untranslated region, the 3'-untranslated region, and the 5' cap region, as well as ribonucleotides which form various secondary structures. Thus, oligonucleotides may be formulated in accordance with this invention which are targeted wholly or in part to these associated ribonucleotides as well as to the coding ribonucleotides. In preferred embodiments, the oligonucleotide is specifically hybridizable with the HCV 5' end hairpin loop, 5' end 6-base-pair repeats, ORF 3 translation initiation codon (all of which are contained in the 5'-untranslated region), polyprotein translation initiation codon, 3'-untranslated region, R2 region, 3' hairpin loop or 3' end palindrome region.

The size of the HCV genome is approximately 9400 nucleotides, with a single translational reading frame encoding a polyprotein which is subsequently processed to several structural and non-structural proteins.

Several regions of the HCV genome have been identified as antisense targets in the present invention. It should be noted that sequence availability and nucleotide numbering schemes vary from strain to strain. The 5' untranslated region of HCV consists of approximately 350 nucleotides upstream of the polyprotein translation initiation codon. A hairpin loop present at nucleotides 1–22 at the 5' end of the genome (HCV-1) identified herein as the "5' end hairpin loop" is believed to serve as a recognition signal for the viral replicase or nucleocapsid proteins. Han et al., *Proc. Natl. Acad. Sci.* 1991, 88, 1711–1715.

Three small (12–16 amino acids each) open reading frames (ORFs) are located in the 5'-untranslated region of HCV RNA. These ORFs may be involved in control of translation. The ORF 3 translation initiation codon as denominated herein is found at nucleotides 315–317 of HCV-1 according to the scheme of Han et al., *Proc. Natl. Acad. Sci.* 1991, 88, 1711–1715; and at nucleotides-127 to -125 according to the scheme of Choo et al., *Proc. Natl. Acad. Sci.* 1991, 88, 2451–2455 and depicted in SEQ ID NO: 25.

The polyprotein translation initiation codon as denominated herein is an AUG sequence located at nucleotides 342–344 of HCV-1 according to Han et al., *Proc. Natl. Acad. Sci.* 1991, 88, 1711–1715 or at nucleotide 1–3 according to the HCV-1 numbering scheme of Choo et al., *Proc. Natl. Acad. Sci.* 1991, 88, 2451–2455 and SEQ ID NO: 25.

The 3' untranslated region, as denominated herein, consists of nucleotides downstream of the polyprotein translation termination site (ending at nt 9037 according to Choo et al. and SEQ ID NO: 25; nt 9377 according to schemes of Han and Inchauspe as depicted in SEQ ID NO: 26). Nucleotides 9697–9716 (numbering scheme of Inchauspe for HCV-H which is depicted in SEQ ID NO: 26) at the 3' terminus of the genome within the 3' untranslated region can be organized into a stable hairpin loop structure identified herein as the 3' hairpin loop. A short nucleotide stretch (R2) immediately upstream (nt 9691–9696 of HCV-H depicted in SEQ ID NO: 26) of the 3' hairpin, and denominated herein "the R2 sequence", is thought to play a role in cyclization of the viral RNA, possibly in combination with a set of 5' end 6-base-pair repeats of the same sequence at nt 23–28 and 38–43. (Inchauspe et al., *Proc. Natl. Acad. Sci.* 1991, 88, 10292–10296) is identified herein as "5' end 6-base-pair repeat". Palindrome sequences present near the 3' end of the genome (nucleotides 9312–9342 according to the scheme of Takamizawa et al., *J. Virol.* 1991, 65, 1105–1113 depicted in SEQ ID NO: 27) are capable of forming a stable secondary structure. This is referred to herein as the 3' end palindrome region.

Oligonucleotides useful in the invention are complementary to HCV RNA. Thus, the oligonucleotides in accordance with the invention preferably have one of the sequences shown in Table 1, or an effective portion thereof. It is preferred to employ any of these oligonucleotides as set forth above or any of the similar oligonucleotides, which persons of ordinary skill in the art can prepare from knowledge of the preferred antisense targets for the modulation of HCV infection.

TABLE 1

RNA SEQUENCE TARGETS AND ANTISENSE OLIGONUCLEOTIDES FOR HCV
[Sequences are from HCV-1 (US) and HCV-J (Japan)]

| SEQ ID NO: | Antisense oligo sequence: | Target description: | Target strand: |
|---|---|---|---|
| 1 | 5'-ATG GTG GAG TGT CGC CCC GTC-3' | 5' end hairpin | + |
| 2 | 5'-GGA GTG ATC TAT GGT GGA GTG-3' | 5' end 6-bp repeat | + |
| 3 | 5'-GAT TCG TGC TCA TGG TGC ACG-3' | Polyprotein AUG | + |
| 4 | 5'-TCC AGG CAT TGA GCG GGT TGA-3' | ORF 3 AUG | + |
| 5 | 5'-TGG CCT GGA GTG TTT ATC TCC-3' | 3'-untranslated | + |
| 6 | 5'-GGG GTA GGC ATC TAC CTG CTC-3' | 3' palindrome | − |
| 7 | 5'-CGC CCC CAT CAG GGG GCT GGC-3' | 5' end hairpin | + |
| 8 | 5'-TTC ATG GTG GAG TGT CGC CCC-3' | 5' end hairpin | + |
| 9 | 5'-GTT CCT CAC AGG GGA GTG ATT-3' | 5' untranslated | + |
| 10 | 5'-TAC TAA CGC CAT GGC TAG ACG-3' | 5' untranslated | + |
| 11 | 5'-CTA TGG CTC TCC CGG GAG GGG-3' | 5' untranslated | + |
| 12 | 5'-CCA CTA TGG CTC TCC CGG GAG-3' | 5' untranslated | + |
| 13 | 5'-CGG TGT ACT CAC CGG TTC CGC-3' | 5' untranslated | + |
| 14 | 5'-CTG GCA ATT CCG GTG TAC TCA-3' | 5' untranslated | + |
| 15 | 5'-GGG GCA CGC CCA AAT CTC CAG-3' | 5' untranslated | + |
| 16 | 5'-CCT TTC GCG ACC CAA CAC TAC-3' | 5' untranslated | + |
| 17 | 5'-CCC TAT CAG GCA GTA CCA CAA-3' | 5' untranslated | + |
| 18 | 5'-CTC CCG GGG CAC TCG CAA GCA-3' | 5' untranstated | + |
| 19 | 5'-CAT GGT GCA CGG TCT ACG AGA-3' | Polyprotein AUG | + |
| 20 | 5'-GAT TCG TGC TCA TGG TGC ACG-3' | Polyprotein AUG | + |
| 21 | 5'-TTT AGG ATT CGT GCT CAT GGT-3' | Polyprotein AUG | + |
| 22 | 5'-GAG TGG TTA GCC CAA TCT TCA-3' | 3' untranslated | + |
| 23 | 5'-TAT GGG CCT GGA GTG GTT AGC-3' | R2 | + |
| 24 | 5'-AGG GAA TGG CCT ATT GGC CTG-3' | R2/3' hairpin | + |

The oligonucleotides of this invention can be used in diagnostics, therapeutics and as research reagents and kits. Since the oligonucleotides of this invention hybridize to RNA from HCV, sandwich and other assays can easily be constructed to exploit this fact. Provision of means for detecting hybridization of oligonucleotide with HCV or HCV RNA present in a sample suspected of containing it can routinely be accomplished. Such provision may include enzyme conjugation, radiolabelling or any other suitable detection systems. Kits for detecting the presence or absence of HCV may also be prepared.

The following specific examples are given for illustrative purposes only and are not intended to limit the invention.

EXAMPLES

Example 1

Oligonucleotide Synthesis

Unmodified DNA oligonucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle is replaced by a 0.2 M solution of 3H-1,2-benzodithiole-3-one 1,1-dioxide in acetonitrile for the stepwise thiation of the phosphite linkages. The thiation cycle wait step is increased to 68 seconds and is followed by the capping step.

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Analytical gel electrophoresis is accomplished in 20% acrylamide, 8 M urea, 45 mM Trisborate buffer, pH 7.0.

Example 2

Transcription and Translation of HCV RNA in Genetically Engineered Cells

A recombinant DNA vector capable of expressing HCV genes in mammalian cells is constructed using standard genetic engineering methods. A cDNA fragment representing the HCV mRNA or genomic transcript is placed behind an inducible eukaryotic promotor such as the LTR from mouse mammary tumor virus in such a way that transcription of the HCV cDNA begins at the appropriate nucleotide position. At the 3' end of the gene, a polyadenylation signal is incorporated to ensure termination at the appropriate nucleotide position. It may be advantageous to modify the coding sequence by insertion of an in-frame reporter domain (e.g., the enzymatically active domain of the firefly luciferase gene) which can simplify detection procedures for expression of the fusion protein. The vector also contains one or more selectable genetic markers such as neomycin resistance.

The described vector is introduced into mammalian cells using a standard calcium chloride transfection procedure. Cells containing transfected DNA are identified by growth in the presence of selective agents such as neomycin, and cloned by limiting dilution. Expression of HCV RNA in cloned transfectants can be verified using any one of a number of assays such as northern blots, RNA polymerase chain reaction, or nuclease protection. Protein expression can be verified using western blotting or immune precipitation with specific HCV antibodies, or by monitoring for the presence of detectable enzymatic activity resulting from the incorporation of an assayable reporter domain. If an inducible promotor such as the MMTV LTR is used in construction of the vector, a glucocorticoid inducer such as dexamethasone should be added to the transfected cells prior to assays in order to induce gene expression.

Example 3
Evaluation of Antisense Oligonucleotide Inhibition of HCV Gene Expression from Genetically Engineered Cells Mammalian cells transfected with expression vectors such as those described in Example 2 are incubated overnight in medium containing antisense oligonucleotides. After oligonucleotide treatment, cells are treated with dexamethasone in order to induce expression of HCV gene products. After a suitable incubation period (4–24 hours) cells are harvested, and expression of specific HCV polypeptide can be detected immunologically using specific antisera in a western blot or immunoprecipitation assay. If the cells contain a vector containing a reporter domain, such as that for firefly luciferase, fused in-frame with the HCV polyprotein, cell extracts can be harvested and evaluated for enzymatic activity of the reporter domain.

Example 4
Transcription and Translation of HCV RNA from Cytoplasmic Virus Vectors A cDNA fragment representing the HCV mRNA or genomic transcript is placed behind a Vaccinia virus promotor in such a way that transcription of the HCV cDNA begins at the appropriate nucleotide position. At the 3' end of the gene, a polyadenylation signal is incorporated to ensure termination at the appropriate nucleotide position. It may be advantageous in some instances to modify the coding sequence by insertion of an in-frame reporter domain (e.g., the enzymatically active domain of the firefly luciferase gene) which can simplify detection procedures for expression of the fusion protein.

Incorporation of the expression unit into the genome of a cytoplasmic replicating DNA virus such as Vaccinia is facilitated by inclusion of sequences upstream and downstream of the expression unit which are homologous to the Vaccinia virus genome. Co-transfection of vector into Vaccinia virus-infected mammalian cells can result in homologous recombination of vector with Vaccinia. If a suitable enzymatic marker such as β-galactosidase is present at the appropriate recombination site in the virus, then recombinant plaques can be identified by a lack of color under appropriate substrate conditions. Cloned virus can be propagated in appropriate host mammalian cell lines and expression of HCV gene products verified as described in Example 2.

Example 5
Evaluation of Antisense Oligonucleotide Inhibition of HCV Gene Expression from Cytoplasmic Virus Vectors in Mammalian Cells Mammalian cells are incubated overnight in medium containing antisense oligonucleotides. After oligonucleotide treatment, cells are infected with recombinant Vaccinia virus expressing HCV gene products. After a suitable incubation period (4–24 hours) cells are harvested, and expression of specific HCV polypeptide can be detected immunologically using specific antisera in a western blot or immunoprecipitation assay. If the cells contain a vector containing a reporter domain, such as that for firefly luciferase, fused in-frame with the HCV polyprotein, cell extracts can be harvested and evaluated for enzymatic activity of the reporter domain.

Example 6
Evaluation of Antisense Oligonucleotide Inhibition of HCV Particle Assembly in Cells Transfected with HCV Genes or Infected with Cytoplasmic Virus Vectors Expressing HCV Genes HCV genomic RNA and protein are expressed in cells transfected with HCV cDNA expression vectors, or in cells infected with Vaccinia virus vectors expressing the HCV cDNA. It is likely that the RNA genomes and proteins will associate to form HCV-like particles. The presence of these particles can be verified using electron microscopy. To evaluate the effects of oligonucleotides complementary to presumed packaging signals of the viral RNA on particle assembly, specific biochemical assays can be developed to measure the appearance of extracellular particles containing both HCV nucleic acid and proteins.

Mammalian cells transfected with expression vectors such as those described in Example 2 are incubated overnight in medium containing antisense oligonucleotides. After oligonucleotide treatment, cells are treated with dexamethasone in order to induce expression of HCV gene products. After a suitable incubation period (4–24 hours) extracellular fluid from treated cells is harvested, and particles are concentrated by pelleting in the ultracentrifuge. Proteins and nucleic acids are extracted from the pellet and quantitated by northern blot and western blot analysis respectively as described in Examples 4 and 5. A similar procedure could be used to monitor effects of oligonucleotide treatment on virus particle assembly resulting from infection of cells with recombinant Vaccinia virus expressing the HCV polyprotein.

What is claimed is:

1. An oligonucleotide 12–25 nucleotides in length which has a nucleotide sequence complementary to at least a portion of a polyprotein translation initiation region of HCV genomic or messenger RNA, said oligonucleotide which inhibits the translation of said RNA.

* * * * *